May 6, 1952 J. J. GRULLEMANS Plant Pat. 1,091
CARYOPTERIS PLANT
Filed Dec. 21, 1950
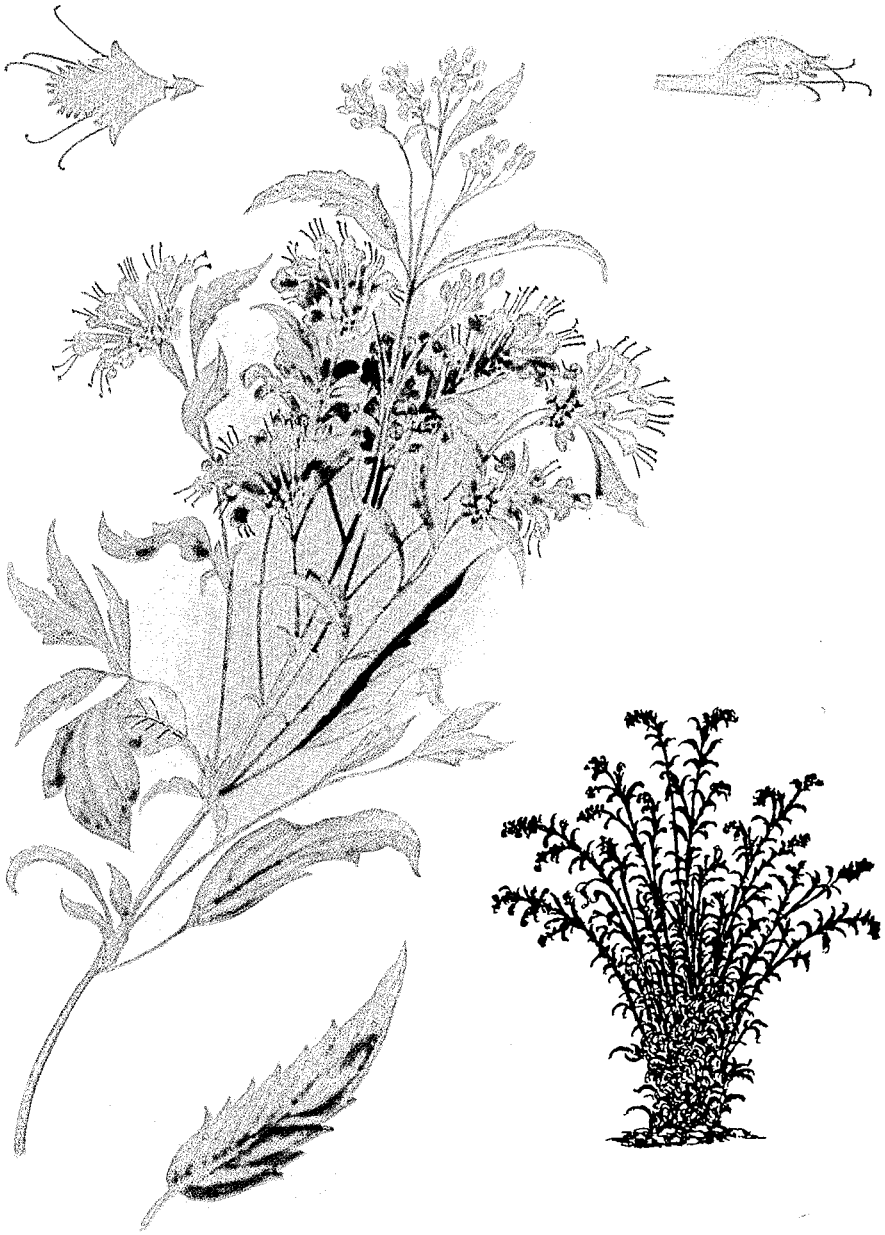
WITNESS
Addison E. Avery
INVENTOR
John J. Grullemans,
by: John H. Leonard,
his ATTY.

Patented May 6, 1952

Plant Pat. 1,091

UNITED STATES PATENT OFFICE 1,091

CARYOPTERIS PLANT

John J. Grullemans, Shaker Heights, Ohio

Application December 21, 1950, Serial No. 201,952

1 Claim. (Cl. 47—60)

This invention relates to a new and distinct variety of Caryopteris plant.

In the drawing:

The large central colored view is an elevational view of a typical terminal of the main stalk of the new variety of Caryopteris plant when the plant is in bloom;

The view at the upper right is an enlarged side elevation of a typical floret of the bloom, the bracts being omitted;

The view at the upper left is an enlarged top plan view of one of the florets;

The view at the lower left is an enlarged top plan view of a typical leaf of the new variety; and The view at the lower right is an elevational view of the exposed plant as a whole, on a reduced scale.

The present variety resulted from the crossing of the variety *Caryopteris clandonensis* commonly known as Blue Mist, an unpatented variety thought to be a cross between the variety Mastacanthus and Incana with a Caryopteris variety of unknown ancestry, of distinct upright growth habit.

The plant was first discovered and grown by me at Mentor, Ohio, in an experimental field in which several hundred hybrids of Caryopteris were being grown and developed, and was asexually reproduced by me from soft wood cuttings.

The plant has the usual fibrous mass root structure of average size, its lateral spread being about equal to the lateral spread of the exposed portion of the plant.

The exposed plant is an herbaceous shrub of generally compact bushy appearance averaging about two and one-half to three feet in height and two to two and one-half feet in spread. It can withstand low temperatures well as compared to other varieties of Caryopteris plant. It prefers intense to moderate sunshine with a generally southerly exposure. It thrives in well-drained poor sandy loam.

The main stalks are upright, slightly curving and much branched and average from two to three feet in length and have a pubescent surface. They are divergent upwardly from the roots but considerably less divergent and recurvant than other varieties of Caryopteris as a result of which the lower portion of the shrub is readily noticeable and not hidden by the recurvant upper portions of the stalks and thus appears columnar and less in diameter relative to the diameter of the open spreading top than is usual in other varieties. As a result the plant presents a more upright, somewhat elongated oval shape.

The branches in general are opposite in arrangement and abundant to average in quantity. The color of the new growth is generally a grayish green though the old growth sometimes shows a reddish tinge.

The leaves are of darker green than average being, on their upper surfaces, a green comparable to Maerz & Paul Pl. No. 23–L–3 or to Ivy Green 000–10–60/3 of the Royal British Horticulture Society Color Chart, and, on their under surfaces, a lighter green comparable to Maerz & Paul Pl. No. 21–D–5 or to Sage Green 000–8–61/2 of the Royal British Horticulture Society Color Chart. They are smooth and somewhat waxy but slightly pubescent on the upper surface as well as the lower surface.

The petioles are of a grayish green averaging about one-quarter inch in length and with a surface which is slightly pubescent. They are of medium strength.

The plant blooms well throughout the United States though it needs winter protection in the extreme North. The best blooms appear to result when the plant is grown in a well-drained neutral sandy loam soil and is exposed directly to the sun. Shade appears to decrease the number of blooms but does not generally affect their size or color. The plant blooms continuously from late August through September.

The florets average about one-quarter inch in diameter with 5,000 to 10,000 per plant and are borne in cymes. About one quarter appear to be in bloom at any given time. The permanence of the blooms on the plants is better than that of the other varieties. The florets have the usual five petals. The color of the florets is unusual, being blue, ranging from a blue comparable to Campanula, Maerz & Paul Pl. 42–J–10 through a blue comparable to Maerz & Paul Pl. 42–J–11. Each floret has a generally white throat and the corolla tube shades to white at its base. The petals are slightly fuzzy and recurvant. The filaments and the pollen of the stamens are blue.

The plant is characterized particularly by its more upright growth due partly to the reduced divergence of the stalks and their reduced recurvancy, thus producing an overall effect of a somewhat smaller diameter compact columnar lower portion which spreads gracefully at the upper portion; the deeper clearer blue color of the individual florets and the bloom as a whole; and the dark green of the leaves which gives the plant an overall dark green tone or effect rather than the usual gray green effect of other varieties of Caryopteris.

Having shown and described my new variety of Caryopteris plant and its mode of asexual reproduction, I claim:

The new and distinct variety of Caryopteris plant as described and illustrated, characterized particularly by the deeper clearer blue color of its bloom, its more upright growth, and the darker green of its leaves.

JOHN J. GRULLEMANS.

No references cited.